United States Patent
Lee et al.

(10) Patent No.: US 11,192,844 B2
(45) Date of Patent: Dec. 7, 2021

(54) METHOD FOR DECOLORIZING AND DEODORIZING POLYHYDRIC ALCOHOL

(71) Applicant: GS CALTEX CORPORATION, Seoul (KR)

(72) Inventors: Jung Joon Lee, Daejeon (KR); Sang Jun Jeon, Daejeon (KR); Hee Geun Nam, Daejeon (KR)

(73) Assignee: GS CALTEX CORPORATION, Seoul (KR)

( * ) Notice: Subject to any disclaimer, the term of this patent is extended or adjusted under 35 U.S.C. 154(b) by 0 days.

(21) Appl. No.: 16/623,477

(22) PCT Filed: Jul. 31, 2018

(86) PCT No.: PCT/KR2018/008674
§ 371 (c)(1),
(2) Date: Dec. 17, 2019

(87) PCT Pub. No.: WO2019/027222
PCT Pub. Date: Feb. 7, 2019

(65) Prior Publication Data
US 2020/0181049 A1    Jun. 11, 2020

(30) Foreign Application Priority Data
Aug. 2, 2017    (KR) .................. 10-2017-0098271

(51) Int. Cl.
*C07C 29/80* (2006.01)
*C07C 29/84* (2006.01)
(Continued)

(52) U.S. Cl.
CPC .............. *C07C 29/80* (2013.01); *B01D 3/002* (2013.01); *B01D 3/143* (2013.01); *B01D 3/148* (2013.01);
(Continued)

(58) Field of Classification Search
CPC ........ C07C 31/18; C07C 31/20; C07C 31/205; C07C 31/207; C07C 29/80
See application file for complete search history.

(56) References Cited

U.S. PATENT DOCUMENTS

| 4,655,879 A * | 4/1987 | Brockmann ........... | B01D 3/148 159/49 |
| 8,399,717 B2 * | 3/2013 | Rousseaux ............. | B01D 3/002 568/868 |

(Continued)

FOREIGN PATENT DOCUMENTS

| CN | 105418367 A | 3/2016 |
| KR | 10-2011-0052257 A | 5/2011 |

(Continued)

OTHER PUBLICATIONS

English translation of KR 2013/0101701 obtained from Espacenet.*
(Continued)

*Primary Examiner* — Jonathan Luke Pilcher
(74) *Attorney, Agent, or Firm* — The PL Law Group, PLLC

(57) ABSTRACT

In a method and a system for decolorizing and deodorizing a polyhydric alcohol according to embodiments of the present invention, a mixture liquid containing a first polyhydric alcohol obtained by a separation process is prepared. The mixture liquid is subjected to a distillation treatment to preliminarily remove substances with different colors and odors to generate a pre-treatment liquid. The pre-treatment liquid is subjected to an adsorption treatment. Through a combination of the distillation treatment and the adsorption treatment, the removing efficiency of the substances with different colors and odors can be increased.

14 Claims, 2 Drawing Sheets

(51) Int. Cl.
*C07C 31/18* (2006.01)
*C07C 31/20* (2006.01)
*B01D 3/14* (2006.01)
*B01D 3/00* (2006.01)
*B01D 15/08* (2006.01)
*B01D 15/36* (2006.01)
*B01D 61/42* (2006.01)
*B01D 3/10* (2006.01)

(52) U.S. Cl.
CPC .......... B01D 15/08 (2013.01); B01D 15/361 (2013.01); B01D 61/422 (2013.01); C07C 29/84 (2013.01); *B01D 3/10* (2013.01); *C07C 31/18* (2013.01); *C07C 31/20* (2013.01); *C07C 31/202* (2013.01); *C07C 31/205* (2013.01); *C07C 31/207* (2013.01)

(56) References Cited

U.S. PATENT DOCUMENTS

| | | | | |
|---|---|---|---|---|
| 9,533,931 | B2* | 1/2017 | Kawamura | C08G 63/183 |
| 10,487,032 | B2* | 11/2019 | Utsunomiya | B01D 3/143 |
| 10,584,084 | B2* | 3/2020 | Kawamura | C12P 7/16 |
| 2011/0257441 | A1* | 10/2011 | Rousseaux | B01D 1/065 |
| | | | | 568/872 |
| 2014/0238841 | A1* | 8/2014 | Kawamura | C12P 7/18 |
| | | | | 203/37 |
| 2014/0275465 | A1* | 9/2014 | Garikipati | C12P 7/18 |
| | | | | 528/68 |
| 2015/0087038 | A1* | 3/2015 | Utsunomiya | C07C 29/80 |
| | | | | 435/158 |
| 2016/0052845 | A1* | 2/2016 | Kawamura | C07C 67/08 |
| | | | | 528/308.8 |

FOREIGN PATENT DOCUMENTS

| | | |
|---|---|---|
| KR | 10-2013-0101701 A | 9/2013 |
| KR | 10-1536934 B1 | 7/2015 |
| KR | 10-1584727 B1 | 1/2016 |
| KR | 10-2016-0018245 A | 2/2016 |
| WO | WO 98/02513 A1 | 1/1998 |
| WO | WO 2010/037843 A1 | 4/2010 |

OTHER PUBLICATIONS

"Equipment for Continuous Distillation", separationprocesses.com, Jun. 13, 2011 (date obtained from WaybackMachine), URL: http://www.separationprocesses.com/Distillation/DT_Chp04a.htm.*
Alviar-Agnew, "SCC: CHEM 330—Adventures in Chemistry"; Aug. 22, 2019; Retrieved Apr. 2, 2021; URL: https://chem.libretexts.org/@go/page/177511.*
International Search Report for PCT/KR2018/008674 dated Nov. 15, 2018.
Office action dated Dec. 22, 2020 from Japan Intellectual Property Office in a counterpart Japanese Patent Application No. 2019-569892 (all the cited references are listed in this IDS.).

* cited by examiner

METHOD FOR DECOLORIZING AND DEODORIZING POLYHYDRIC ALCOHOL

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/008674, filed on Jul. 31, 2018, which claims priority to the benefit of Korean Patent Application No. 10-2017-0098271 filed in the Korean Intellectual Property Office on Aug. 2, 2017, the entire contents of which are incorporated herein by reference.

TECHNICAL FIELD

The present invention relates to a method of decolorizing and deodorizing a polyhydric alcohol. More particularly, the present invention relates to a method of decolorizing and deodorizing a polyhydric alcohol after a separation process.

BACKGROUND ART

Polyhydric alcohols are compounds having more than one hydroxyl group (—OH) in one molecule. Among these, a dihydric alcohol is called glycol, and a trihydric alcohol is called glycerol. Polyhydric alcohols are used as hydrophilic and protic solvents, and used in various applications for cosmetic compositions, pharmaceutical additives, and antifreeze liquids for automobiles.

For example, 2,3-butanediol has been widely used as a raw material or additive for electronic material additives, insecticides, cosmetics and beauty products, and has increased utilization in the medical field because of chirality.

2,3-butanediol may be produced by a chemical method such as hydration of 2,3-buteneoxide, or synthesized by a biological fermentation process to obtain 2,3-butanediol with a specific optical activity.

It is necessary to produce colorless and odorless 2,3-butanediol to be applied for cosmetics and medicines, a 2,3-butanediol crude liquid may have a yellowish color and bad odor due to a small amount of impurities which have not been removed in separation and purification processes.

In addition, when 2,3-butanediol is synthesized using biological processes using microorganisms and strains, various kinds of materials with undesirable colors and odors derived from proteins or biomass may be contained.

For example, in Chinese Unexamined Patent Application No. 105418367, a method of removing a pigmentation-causing material by treating a 2,3-butanediol crude liquid with activated carbon is disclosed. However, there is a limit to removing all materials causing undesirable colors and odors from a 2,3-butanediol crude liquid only by activated carbon treatment.

SUMMARY

The present invention is directed to providing a method of decolorizing and deodorizing a polyhydric alcohol having high efficiency and removal capacity.

The present invention is also directed to providing a system for decolorizing and deodorizing a polyhydric alcohol with high efficiency and removal capacity.

1. A method of decolorizing and deodorizing a polyhydric alcohol, which includes: preparing a mixed liquid containing a first polyhydric alcohol obtained by a separation process; producing a pre-treatment liquid by preliminarily removing materials with undesirable colors and odors through distillation treatment of the mixed liquid; and adsorbing the pre-treatment liquid.

2. The method according to 1, wherein the mixed liquid includes the first polyhydric alcohol, water and a neutralizing agent.

3. The method according to 2, wherein the neutralizing agent includes at least one of a carbonate and a metal hydroxide.

4. The method according to 2, wherein the neutralizing agent is contained at 0.1 to 1 part by weight with respect to 100 parts by weight of the first polyhydric alcohol.

5. The method according to 1, wherein the distillation treatment includes fractional distillation treatment and stripping treatment.

6. The method according to 5, wherein the fractional distillation treatment is directly performed on the mixed liquid, and the stripping treatment is performed on a second polyhydric alcohol obtained after the fractional distillation treatment.

7. The method according to 6, wherein the stripping treatment includes injecting water or steam into the second polyhydric alcohol and then removing the water using a distillation column or simple distillation.

8. The method according to 7, wherein the amount of water or steam added in the stripping treatment is 40 to 200 parts by weight with respect to 100 parts by weight of the second polyhydric alcohol.

9. The method according to 6, wherein the stripping treatment further includes purging with air or nitrogen.

10. The method according to 6, wherein the fractional distillation treatment further includes discharging an initial fluid from a distillation column.

11. The method according to 10, wherein the fractional distillation treatment further includes removing a residue collected in the lower part of the distillation column.

12. The method according to 1, wherein the adsorption treatment includes treating the pre-treatment liquid with activated carbon.

13. The method according to 12, wherein the activated carbon is treated using activated carbon powder or an activated carbon-fixed bed.

14. The method according to 13, further comprising, when the activated carbon powder is used, separating the activated carbon from an adsorption-treated liquid.

15. The method according to 12, wherein the adsorption treatment further includes adding 10 to 100 parts by weight of water with respect to 100 parts by weight of the pre-treatment liquid.

16. The method according to 15, further comprising performing reduced pressure evaporation of the adsorption-treated liquid.

17. The method according to 1, wherein the separation process includes at least one of ion exchange treatment, electrodialysis and reduced pressure distillation of a polyhydric alcohol fermentation broth.

18. The method according to 17, wherein the polyhydric alcohol fermentation broth includes 2,3-butanediol synthesized from biomass.

19. A system for decolorizing and deodorizing a polyhydric alcohol, which includes a fractional distillation unit for distillation treatment of a first polyhydric alcohol obtained by a separation process; a stripping unit for distillation treatment of a second polyhydric alcohol supplied from the fractional distillation unit; and an adsorption unit for removal of materials with undesirable colors and odors remaining in the polyhydric alcohol supplied from the stripping unit.

According to exemplary embodiments of the present invention, in a process of decolorizing/deodorizing a polyhydric alcohol produced by a separation/purification process, distillation treatment can be performed before adsorption treatment such as activated carbon treatment. Therefore, as materials with undesirable colors and odors are removed by an evaporation or fractional distillation mechanism, a load in the adsorption treatment can be reduced, and the removal efficiency/removal capacity of materials with undesirable colors and odors can be increased.

The distillation treatment can include a multi-step process. The distillation treatment can include fractional distillation treatment and stripping treatment. The materials with undesirable colors and odors can be removed in a bulk unit due to the difference in boiling point through the fractional distillation treatment, and remaining materials with undesirable colors and odors can be removed in a smaller unit through the stripping treatment.

According to adsorption treatment performed after the distillation treatment, a colorless and odorless polyhydric alcohol from which materials with undesirable colors and odors are substantially and completely removed can be obtained. For example, substantially colorless and odorless 2,3-butanediol can be produced from a 2,3-butanediol synthetic liquid containing numerous impurities and materials with undesirable colors and odors through biological synthesis.

DETAILED DESCRIPTION

Hereinafter, preferred embodiments of the present invention will be suggested. However, the embodiments are merely provided to exemplify the present invention, not to limit the scope of the present invention, and all alternatives and modifications within the scope of the accompanying claims are included in the present invention.

Figure 1:
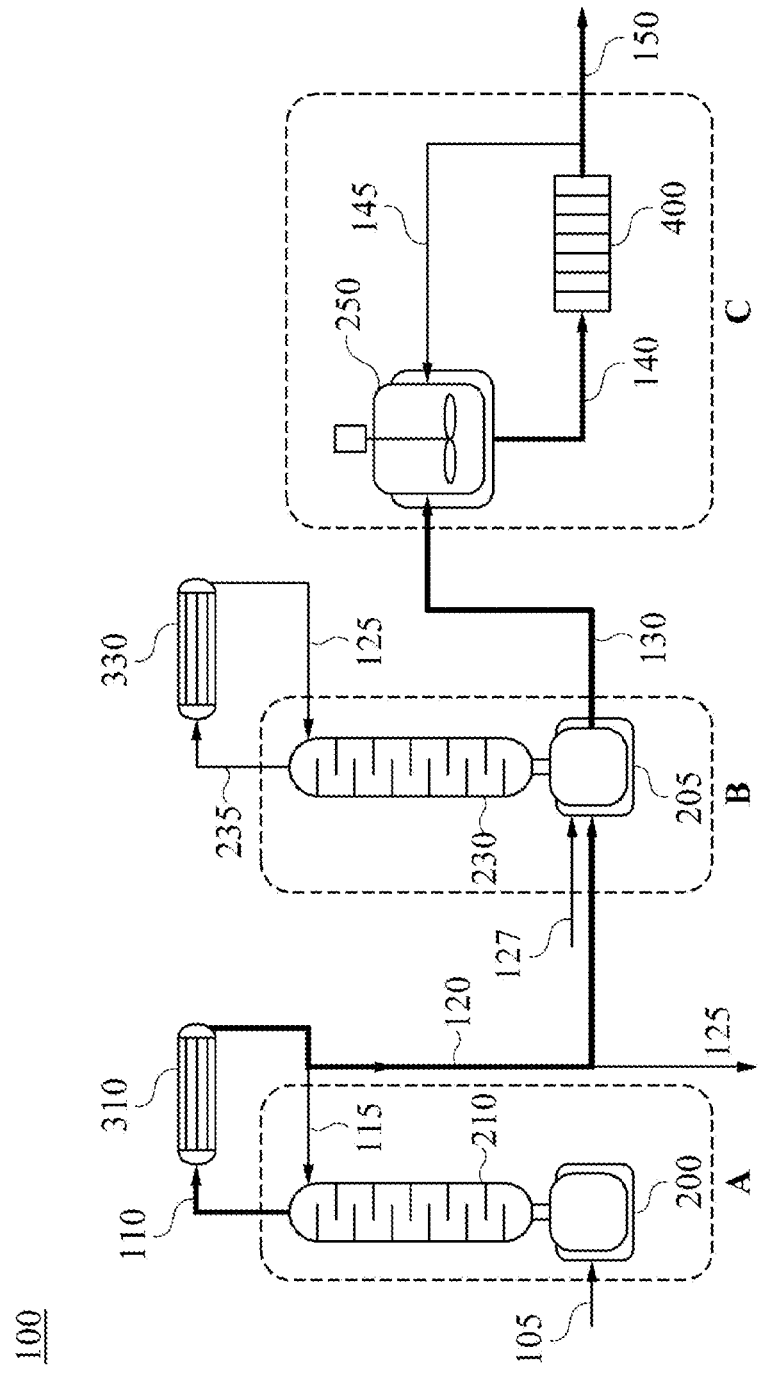
FIG. 1 is a conceptual diagram for illustrating a system for decolorizing and deodorizing a polyhydric alcohol according to exemplary embodiments of the present invention.
Figure 2:
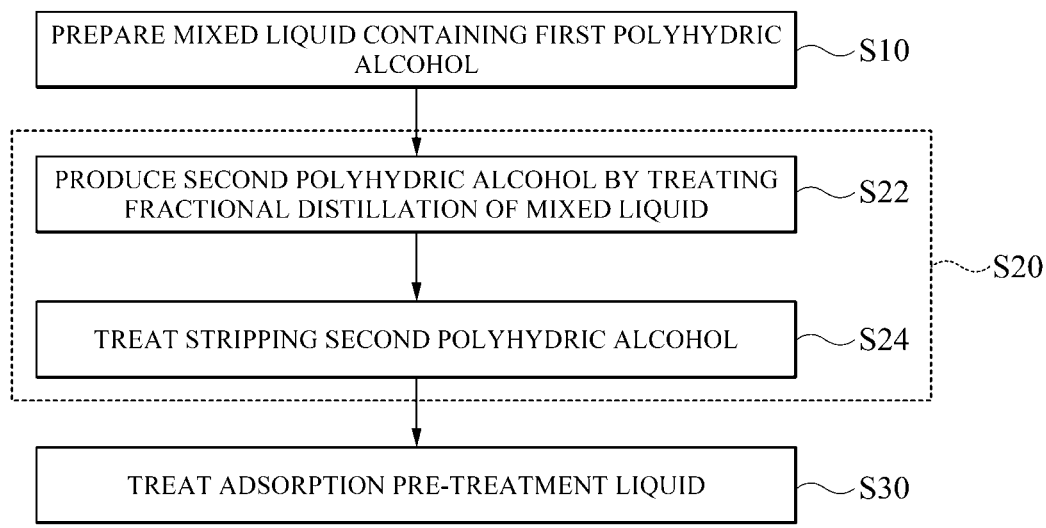
FIG. 2 is a process flow diagram illustrating a method of decolorizing and deodorizing a polyhydric alcohol according to exemplary embodiments of the present invention.

FIG. 1 is a conceptual diagram for illustrating a system for decolorizing and deodorizing a polyhydric alcohol according to exemplary embodiments of the present invention. FIG. 2 is a process flow diagram illustrating a method of decolorizing and deodorizing a polyhydric alcohol according to exemplary embodiments of the present invention.

Hereinafter, referring to FIGS. 1 and 2, a system and method for decolorizing and deodorizing a polyhydric alcohol are explained together.

Referring to FIG. 1, a system 100 for decolorizing and deodorizing a polyhydric alcohol (hereinafter, can be shortened as "system") according to exemplary embodiments may include a distillation unit and an adsorption unit C. According to exemplary embodiments, the distillation unit may include a fractional distillation unit A and a stripping unit B.

The fractional distillation unit A may include a first storage 200 and a fractional distillation column 210. The stripping unit B may include a second storage 205 and a stripping column 230. The adsorption unit C may include an adsorption treatment chamber 250.

Referring to FIG. 2, a first mixed liquid containing a first polyhydric alcohol may be prepared (S10). According to exemplary embodiments, the first polyhydric alcohol may be a polyhydric alcohol collected after a separation process for a polyhydric alcohol fermentation broth.

In some embodiments, the polyhydric alcohol fermentation broth may be prepared by fermenting a bio-raw material (or a biomass) using a strain. The bio-raw material may be cereals (kernel), lignocellulosic and/or starch materials. In exemplary embodiments, starch materials may be used as the bio-raw materials, and examples of the starch materials may include starch-containing cereals such as corn, oats, etc., cassava, raw-sugar, glucose, etc.

As the strain, for example, microorganisms having an ability to produce a diol-containing fermentation product may be used without particular limitation. For example, the microorganisms may be *Klebsiella, Bacillus, Serratia, Enterobacter, Clostridium*, yeast, or *E. coli*.

The bio-raw material and the strain may be selected in consideration of a target diol of interest. In exemplary embodiments of the present invention, the target diol may be 2,3-butanediol. In an embodiment, the target diol may include 2R,3S-butanediol of the optical isomers of 2,3-butanediol.

In some embodiments, to produce 2,3-butanediol, as the bio-raw material, cassava, and as the strain, *Klebsiella* may be used. For example, as the strain, *Klebsiella oxytoca* (*K. oxytoca*) or *Klebsiella pneumoniae* (*K. pneumoniae*) may be used, and preferably, *K. oxytoca* is used.

According to exemplary embodiments, the polyhydric alcohol fermentation broth may be prepared by a saccharification process and a fermentation process. For example, after the bio-raw material is grinded, a hydrolysate may be prepared by grinding the bio-raw material, mixing the grinded material in a liquid such as fresh water, and reacting the resulting mixture with the bio-raw material. The saccharification enzyme may include, for example, an amylase family enzyme.

Afterward, a fermentation broth may be prepared by adding the strain to the hydrolysate. The fermentation broth may include monoalcohols and other glycols (e.g., ethylene glycol, diethylene glycol, 1,3-propanediol, 1,2-propylene glycol, and dipropylene glycol) as well as 2,3-butanediol as a target diol. In addition, the fermentation broth may include all kinds of inorganic salts, organic acids, and impurities causing undesirable colors and odors, such as bio by-products derived from the microbial strain or a metabolic product thereof.

The separation process may include a process for selectively collecting a target diol of interest. For example, the separation process may include an ion exchange process, an electrodialysis process, and a vacuum distillation process.

The decolorizing and deodorizing method and system according to embodiments of the present invention may be a process and process system which may be performed after the separation process.

According to exemplary embodiments, the first mixed liquid may include the first polyhydric alcohol (e.g., 2,3-butanediol), water and a neutralizing agent. In addition, materials with undesirable colors and odors which are not removed in the separation process may be included in the first mixed liquid.

In some embodiments, the neutralizing agent may include a carbonate and/or a metal hydroxide. As non-limiting examples of the carbonate, $NaHCO_3$, $KHCO_3$, $Na_2CO_3$, $K_2CO_3$, and $CaCO_3$ may be included, and they may be used alone or in combination of two or more thereof. As non-limiting examples of the metal hydroxide, NaOH, $Ca(OH)_2$, and $Mg(OH)_2$ may be used, and they may be used alone or in combination of two or more thereof.

The carbonate or metal hydroxide may adjust a pH of the first mixed liquid, and acid materials such as organic acids and inorganic acids, which are present in the first mixed liquid, may be removed by a neutralization or precipitation reaction. In addition, the removal of materials with undesirable colors and odors because of the difference in boiling point may be promoted through the addition of carbonate(s). Accordingly, the efficiency of removing materials with undesirable colors and odors in the distillation unit may be improved.

In some embodiments, a monovalent carbonate and a bivalent carbonate may be used together for neutralization efficiency. For example, $KHCO_3$ and $CaCO_3$ may be used together as the neutralizing agent.

In an embodiment, the neutralizing agent may be included at approximately 0.1 to 1 part by weight with respect to 100 parts by weight of the first polyhydric alcohol included in the first mixed liquid. When the content of the neutralizing agent is approximately less than 0.1 part by weight, the above-described acid removal effect may be insufficiently exhibited. When the content of the neutralizing agent is approximately more than 1 part by weight, the amount of a residue generated after fractional distillation is finished may increase, thereby lowering a recovery rate.

In the first mixed liquid, water may be included at approximately 5 to 10 parts by weight with respect to 100 parts by weight of the first polyhydric alcohol. When the water content is approximately less than 5 parts by weight, impurities containing materials with undesirable colors and odors may be insufficiently dissolved. When the water content is approximately more than 10 parts by weight, a process yield and efficiency may be lowered.

Non-limiting examples of the materials with undesirable colors and odors may be acetaldehyde, acetoin, diacetyl, furfural and methanol.

At least some of the materials with undesirable colors and odors in the first mixed liquid may be removed by distillation treatment (S20). According to exemplary embodiments, the distillation treatment may include fractional distillation treatment and stripping treatment.

The first mixed liquid may be directly supplied to the fractional distillation unit A and subjected to by fractional distillation treatment, thereby producing a second polyhydric alcohol (S22). The second polyhydric alcohol may refer to an alcohol liquid prepared by removing at least some of materials with undesirable colors and odors from the first polyhydric alcohol.

The first mixed liquid may be introduced into a first storage 200 included in the fractional distillation unit A through a first supply line 105. The first supply line 105 may be connected to a device, chamber or column for the separation process, such that the first polyhydric alcohol may be supplied thereto.

The first mixed liquid supplied to the first storage 200 is supplied to a fractional distillation column 210, and the first polyhydric alcohol is discharged from the upper part of the fractional distillation column 210 through a first discharge line 110 due to the difference in boiling point, thereby obtaining the second polyhydric alcohol.

For example, the boiling point of the first polyhydric alcohol may be lower than those of the materials with undesirable colors and odors, and thus the first polyhydric alcohol may be separated and discharged from the top part of the fractional distillation column 210.

For example, in the fractional distillation column 210, a temperature for separating and discharging the first polyhydric alcohol may be 60 to 80° C., and a pressure may be maintained in a range from 7 to 10 mbar.

The second polyhydric alcohol discharged through the first discharge line 110 may be condensed by a first condenser 310 and transferred through a second supply line 120.

In some embodiments, an initial fluid discharged from the fractional distillation column 210 may be removed to the outside through a second discharge line 125 branched from the second supply line 120. For example, in the early stage of the fractional distillation, the polyhydric alcohol and impurities (including materials with undesirable colors and odors) may be evaporated and discharged with the first polyhydric alcohol because of intermolecular interactions despite the difference in boiling point. Therefore, as the initial fluid is discharged and removed, the purity of the second polyhydric alcohol may be improved.

In an embodiment, the initial fluid may be refluxed back to the fractional distillation column 210 through a first recovery line 115 connected with the first condenser 310. In this case, the yield of the target polyhydric alcohol may be improved, and the amount of a process by-product or waste may be reduced.

In the first storage 200, a residue of the first mixed liquid which has not been treated after the above-described fractional distillation treatment may be stored. The residue may be removed or discharged to the outside from the fractional distillation unit A, thereby improving the purity of the second polyhydric alcohol.

For example, by removing the initial fluid and/or the residue, with respect to 100 parts by weight of the total polyhydric alcohol included in the first mixed liquid, approximately 85 to 90 parts by weight of the second polyhydric alcohol may be produced.

Afterward, stripping treatment may be performed on the second polyhydric alcohol supplied from the second supply line 120 to the stripping unit B (S24)

According to exemplary embodiments, a second mixed liquid prepared by adding water to the second polyhydric alcohol may be supplied to the second storage 205. For example, the second mixed liquid mixed with the second polyhydric alcohol may be produced by supplying water into the second storage 205 through a water supply line 127.

In some embodiments, a second mixed liquid mixed with the second polyhydric alcohol may be produced by supplying steam to the second storage 205.

In some embodiments, with respect to 100 parts by weight of the second polyhydric alcohol, the water or steam content may be approximately 40 to 200 parts by weight according to the number of columns used herein. When the amount of the added water or stream is approximately less than 40 parts by weight, it may not be easy to remove the materials with undesirable colors and odors by the stripping treatment. When the amount of the added water or steam is approximately more than 200 parts by weight, a load in the stripping unit B excessively increases, and the productivity and yield of the target alcohol may be reduced.

The second mixed liquid may be supplied from the second storage 205 to the stripping column 230 for stripping treatment. The materials with undesirable colors and odors remaining in the second mixed liquid may be evaporated and removed with water through the stripping treatment.

According to exemplary embodiments, the stripping treatment may be performed at a temperature which is lower than the boiling point of the target polyhydric alcohol and higher than the boiling point of water. In addition, the stripping treatment may be performed at a temperature lower than the temperature (e. g, the maximum temperature in the fractional distillation treatment) for the fractional distillation treatment.

For example, the stripping treatment may be performed at approximately 20 to 30° C. and under a pressure of approximately 15 to 25 mbar.

According to an exemplary embodiment, in addition to using the stripping column 230, a process of removing water through simple distillation may be used for the stripping treatment.

Through the stripping treatment, materials with undesirable colors and odors which are difficult to be removed due to the difference in boiling point in the fractional distillation may be removed by interactions such as hydrogen bonding with water.

In an embodiment, ppm-level materials with undesirable colors and odors may be removed by the stripping treatment. In an embodiment, micro materials with undesirable odors, which have not been removed by the fractional distillation treatment, may be further removed by the stripping treatment.

In an embodiment, the removal of the materials with undesirable colors and odors may be promoted by purging with air or nitrogen during the stripping treatment.

Water containing the materials with undesirable colors and odors may be evaporated and extracted from the upper part (e.g., top) of the stripping column 230, and then discharged through a second discharge line 235.

In one embodiment, water discharged from the second discharge line 235 may be refluxed into the stripping column 230 via a second condenser 330 and a second recovery line 125. In this case, the target polyhydric alcohol partially contained in water may be recovered, and thus the production yield may be improved.

A pre-treatment liquid in which a target polyhydric alcohol is more concentrated or purified than the second mixed liquid may be produced by removing at least some of materials with undesirable colors and odors from the second mixed liquid through evaporation.

Afterward, remaining materials with undesirable colors and odors may be further removed by adsorption treatment of the pre-treatment liquid (S30). In some embodiments, the materials with undesirable colors and odors may be substantially and completely removed through the adsorption treatment.

The pre-treatment liquid may be supplied to an adsorption treatment chamber 250 of an adsorption unit C through a third supply line 130 connected with the second storage 205.

For example, an adsorbent may be brought into contact or mixed with the pre-treatment liquid in the adsorption treatment chamber 250. According to exemplary embodiments, the adsorbent may contain activated carbon.

For example, the activated carbon powder put into the adsorption treatment chamber 250 may be brought into contact with the pre-treatment liquid by stirring, and remaining materials with undesirable colors and odors may be removed.

To activate the adsorption reaction, 10 to 100 parts by weight of water may be added with respect to 100 parts by weight of the pre-treatment liquid, and the temperature in the adsorption treatment chamber 250 may be maintained at approximately 70 to 90° C.

The activated carbon may be used at 0.3 to 1.0 part by weight with respect to 100 parts by weight of the pre-treatment liquid. Although a relatively small amount of the activated carbon is used compared to the conventional process, the removal of materials with undesirable colors and odors may be efficiently performed.

In some embodiments, the adsorption treatment chamber 250 may include a bed or column to which the activated carbon is fixed. When the activated carbon-fixed bed or column is used, the system may further include a washing part for washing the bed or column.

When the activated carbon powder is used as an adsorbent, a process of separating activated carbon to which the materials with undesirable colors and odors are adsorbed may be further performed. For example, an adsorption-treated liquid containing a target polyhydric alcohol may be supplied from the adsorption treatment chamber 250 to a filtering part 400 through a fourth supply line 140. The activated carbon is filtered together with the materials with undesirable colors through the filter part 400, and a substantially colorless and odorless target polyhydric alcohol may be obtained with high purity through a collection line 150.

In some embodiments, the treatment liquid discharged from the filtering part 400 may be recycled to the adsorption treatment chamber 250 through a third recovery line 145, and thus adsorption treatment may be repeatedly performed.

In some embodiments, when water is added in the adsorption treatment, components with undesirable colors and odors may be further removed by removing water from the adsorption-treated liquid discharged from the filtering part 400 through reduced pressure evaporation.

Hereinafter, with reference to specific experimental examples, a method of decolorizing and deodorizing a polyhydric alcohol according to embodiments of the present invention will be described in detail. Examples and comparative examples included in the experimental examples are merely provided to exemplify the present invention and do not limit the accompanying claims. However, it is obvious that the examples can be changed and modified in various ways within the scope and technical idea of the present invention, and such variations and modifications are also included within the scope of the accompanying claims.

EXAMPLES AND COMPARATIVE EXAMPLES

Example 1

A polyhydric alcohol fermentation broth containing 2,3-butanediol was obtained using a *K. oxytoca* GSC112 LK strain by grinding and saccharifying cassava as a raw material, and then the fermentation broth was subjected to filtration, electrodialysis, ion exchange and distillation, thereby obtaining 2,3-butanediol (first polyhydric alcohol). A first mixed liquid in which 0.4 part by weight of $K_2CO_3$ and 5 parts by weight of water were mixed with respect to 100 parts by weight of the 2,3-butanediol (first polyhydric alcohol) was prepared, and 90 parts by weight of a polyhydric alcohol (second polyhydric alcohol) was extracted from the upper part of a reduced pressure fractional distillation column at the maximum temperature of 80° C.

Afterward, 40 parts by weight of water was added with respect to 100 parts by weight of the second polyhydric alcohol to perform stripping using a stripping column at 24° C., and a pre-treatment liquid remaining in the lower part was supplied into a chamber containing 0.3 part by weight of activated carbon and 10 parts by weight of ultrapure water with respect to 100 parts by weight of the pre-treatment liquid and stirred at 500 rpm for 30 minutes at 80° C.

Finally, 2,3-butanediol was obtained by filtering the adsorption treated liquid through a filter.

Example 2

The pre-treatment liquid which had been subjected to stripping in Example 1 was supplied into a chamber containing 0.6 part by weight of activated carbon and 100 parts by weight of ultrapure water with respect to 100 parts by weight of the pre-treatment liquid, and stirred at 500 rpm for 30 minutes at 80° C.

After stirring, the adsorption-treated liquid was filtered through a filter, and the filtrate was subjected to reduced pressure evaporation to remove water at 24° C. under 13 mbr, thereby finally obtaining 2,3-butanediol.

Comparative Example

The first polyhydric alcohol, which is the same as in Example 1, was supplied and stirred in a treatment chamber containing 50 parts by weight of water and 5 parts by weight of activated carbon with respect to 100 parts by weight of the first polyhydric alcohol and subjected to reduced pressure evaporation to remove water at 50° C. under 40 mbar, there by obtaining 2,3-butanediol under a 10 mbr condition.

Experimental Example

The purity (area ratio) of 2,3-butanediol was measured by gas chromatography performed on the 2,3-butanediol liquids obtained according to Examples and Comparative Example. Specifically, gas chromatography analysis was performed using Agilent 6890 GC-MS (column: HP-5MS).

For quality evaluation, an APHA color index for colors of the 2,3-butanediol liquids obtained according to Examples and Comparative Example was measured. In addition, the average score of 30 panelists was calculated by sensory evaluation for the expression of undesirable odors according to the following evaluation criteria. The evaluation result is shown in Table 1 below.

<Evaluation of Undesirable Odors>
1: Generation of strong undesirable odor
2: Generation of medium-level undesirable odor
3: Generation of weak undesirable odor for a short time
4: No odor

TABLE 1

|  | Purity of 2,3-butanediol (area ratio) | Color evaluation (APHA color) | Undesirable odor evaluation |
| --- | --- | --- | --- |
| Example 1 | 99.8% | 0 | 3.5 |
| Example 2 | 99.8% | 0 | 4 |
| Comparative Example | 99.8% | 5 | 1.8 |

Referring to Table 1, in Examples subjected to distillation, compared to Comparative Example, removal amounts of the materials with undesirable colors and odors significantly increased.

In Example 2 in which water was added in the adsorption of activated carbon and then removed through reduced pressure evaporation, it can be seen that the materials with undesirable colors and odors were substantially and completely removed.

The invention claimed is:

1. A method of decolorizing and deodorizing a polyhydric alcohol, comprising:

preparing a first mixed liquid containing a polyhydric alcohol and material with an undesirable color and an odor, the polyhydric alcohol obtained by separating the polyhydric alcohol from a polyhydric alcohol fermentation broth;

treating the first mixed liquid with a fractional distillation to remove at least a part of the material with the undesirable color and odor;

producing a second mixed liquid by adding an amount of water to the treated first mixed liquid;

producing a pre-treatment liquid, in which the polyhydric alcohol is more concentrated or purified than the second mixed liquid, by performing a stripping treatment to the second mixed liquid to evaporate with the water at least a part of the material with the undesirable color and odor remaining in the second mixed liquid by interactions with the water, wherein the stripping treatment is performed at a temperature lower than a boiling point of the polyhydric alcohol and higher than a boiling point of the water; and performing an adsorption treatment by contacting the pre-treatment liquid with an adsorbent to remove the material with the undesirable color and odor remaining in the pre-treatment liquid, wherein the amount of water added before the stripping treatment is 40 to 200 parts by weight with respect to 100 parts by weight of the polyhydric alcohol.

2. The method of claim 1, wherein the first mixed liquid contains the polyhydric alcohol, water and a neutralizing agent.

3. The method of claim 2, wherein the neutralizing agent contains at least one of a carbonate and a metal hydroxide.

4. The method of claim 2, wherein the neutralizing agent is contained at 0.1 to 1 part by weight with respect to 100 parts by weight of the polyhydric alcohol.

5. The method of claim 1, wherein the stripping treatment further comprises purging with air or nitrogen.

6. The method of claim 1, wherein the fractional distillation treatment further comprises removing an initial fluid first discharged from a distillation column.

7. The method of claim 6, wherein the fractional distillation treatment further comprises removing a residue collected in the lower part of the distillation column.

8. The method of claim 1, wherein the adsorption treatment comprises treating the pre-treatment liquid with activated carbon.

9. The method of claim 8, wherein the activated carbon comprises at least one of activated carbon powder and an activated carbon-fixed bed.

10. The method of claim 9, further comprising, when the activated carbon powder is used, separating the activated carbon from an adsorption-treated liquid.

11. The method of claim 8, wherein the adsorption treatment further comprises adding 10 to 100 parts by weight of water with respect to 100 parts by weight of the pre-treatment liquid.

12. The method of claim 11, further comprising performing reduced pressure evaporation of adsorption-treated liquid.

13. The method of claim 1, wherein the separating comprises at least one of ion exchange treatment, electrodialysis and reduced pressure distillation of the polyhydric alcohol fermentation broth.

14. The method of claim 13, wherein the polyhydric alcohol fermentation broth comprises 2,3-butanediol synthesized from biomass.

* * * * *